United States Patent
Thornton (10) Patent No.: US 8,236,216 B2
(45) Date of Patent: Aug. 7, 2012

(54) SYSTEM AND METHOD FOR FORMING A CUSTOM MEDICAL MASK USING AN ORIENTATION DEVICE

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 1351 days.

(21) Appl. No.: 11/768,474

(22) Filed: Jun. 26, 2007

(65) Prior Publication Data

US 2008/0006274 A1    Jan. 10, 2008

Related U.S. Application Data

(60) Provisional application No. 60/806,662, filed on Jul. 6, 2006.

(51) Int. Cl.
*B29C 33/40* (2006.01)
(52) U.S. Cl. ...................................................... 264/222
(58) Field of Classification Search .................. 264/222
See application file for complete search history.

(56) References Cited

U.S. PATENT DOCUMENTS

| | | |
|---|---|---|
| 339,334 A | 4/1886 | Searle |
| 690,663 A | 1/1902 | Pratt |
| 746,869 A | 12/1903 | Moulton |
| 774,446 A | 11/1904 | Moulton |
| 781,516 A | 1/1905 | Guthrie, Jr. |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |

(Continued)

FOREIGN PATENT DOCUMENTS

DE            156627          12/1904

(Continued)

OTHER PUBLICATIONS

Japanese Patent Office Action re Appln. 2004-500750, mailed Oct. 14, 2008.

(Continued)

*Primary Examiner* — Larry Thrower
(74) *Attorney, Agent, or Firm* — Baker Botts L.L.P.

(57) ABSTRACT

According to one embodiment, forming a custom medical mask includes, while an oral appliance is positioned in a user's mouth to receive the user's teeth and is coupled to an orientation device, applying an impression material over the device and the user's face, such that the impression material conforms to the device and to the user's unique facial features. The impression material may be removed together with the device and a cast may be created using the impression material together with the device as a mold, such that the cast conforms to the impression material and the device. A deformable material may be applied to the cast to form a custom medical mask for the user, such that the deformable material conforms to the cast. The custom medical mask is custom-fitted to the user's unique facial features and custom-oriented to the user's teeth.

13 Claims, 7 Drawing Sheets

U.S. PATENT DOCUMENTS

| | | | |
|---|---|---|---|
| 1,675,202 A | 6/1928 | Warne | |
| 1,679,748 A | 8/1928 | Stratton | |
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,671,446 A | 3/1954 | Mann | 128/163 |
| 2,712,160 A | 7/1955 | Sterczek | 18/55.05 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 2,917,045 A | 12/1959 | Schildknecht et al. | 128/141 |
| 2,977,636 A | 4/1961 | McGuire | 18/58.7 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,330,274 A | 7/1967 | Bennett | 128/146.7 |
| 3,360,860 A | 1/1968 | Roland | 32/17 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,695,265 A | 10/1972 | Brevik | 128/146.2 |
| 3,845,768 A | 11/1974 | Garrahan | 128/142.7 |
| 3,854,208 A | 12/1974 | Arant | 32/19 |
| 3,864,832 A | 2/1975 | Carlson | 32/40 R |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205.12 |
| 4,258,710 A | 3/1981 | Reber | |
| 4,289,127 A | 9/1981 | Nelson | 128/207.14 |
| 4,294,243 A | 10/1981 | Ernsting et al. | 128/201.18 |
| 4,304,227 A | 12/1981 | Samelson | 128/136 |
| 4,345,592 A | 8/1982 | Giorgini et al. | 128/204.26 |
| 4,345,593 A | 8/1982 | Sullivan | 128/204.26 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202.27 |
| 4,397,701 A | 8/1983 | Johnson et al. | 156/62 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A | 6/1984 | Saumell | 264/154 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,741,696 A | 5/1988 | Cetlin | |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,605 A | 8/1989 | Levy | |
| 4,858,606 A | 8/1989 | Hamlin | 128/204.29 |
| 4,862,903 A | 9/1989 | Campbell | 128/861 |
| 4,870,962 A | 10/1989 | Sitnik | 128/205.13 |
| 4,886,056 A | 12/1989 | Simpson | 128/201.25 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,941,212 A | 7/1990 | Liff | 2/206 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,062,421 A | 11/1991 | Burns et al. | 128/205.27 |
| 5,064,371 A | 11/1991 | Smeltzer | 433/37 |
| 5,065,756 A | 11/1991 | Rapoport | 128/204.18 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204.25 |
| 5,213,498 A | 5/1993 | Pelerin | 433/37 |
| 5,233,978 A | 8/1993 | Callaway | 128/205.25 |
| 5,243,971 A | 9/1993 | Sullivan et al. | 128/205.25 |
| 5,243,972 A | 9/1993 | Huang | |
| 5,245,995 A | 9/1993 | Sullivan et al. | 128/204.23 |
| 5,265,595 A | 11/1993 | Rudolph | |
| 5,267,557 A | 12/1993 | Her-Mou | 128/206.21 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,336,086 A | 8/1994 | Simmen et al. | |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,392,773 A | 2/1995 | Bertrand | 128/206.11 |
| 5,409,017 A | 4/1995 | Lowe | |
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204.23 |
| 5,474,060 A | 12/1995 | Evans | |
| 5,477,850 A | 12/1995 | Zegler et al. | 128/202.11 |
| 5,499,633 A | 3/1996 | Fenton | |
| 5,503,146 A | 4/1996 | Froehlich et al. | 128/204.23 |
| 5,503,552 A | 4/1996 | Diesso | |
| 5,517,983 A | 5/1996 | Deighan et al. | 128/204.23 |
| 5,537,994 A | 7/1996 | Thornton | 128/204.18 |
| 5,537,999 A | 7/1996 | Dearman et al. | 128/205.25 |
| 5,538,000 A | 7/1996 | Rudolph | 128/205.25 |

| | | | |
|---|---|---|---|
| 5,538,014 A | 7/1996 | Wilson et al. | 128/863 |
| 5,540,223 A | 7/1996 | Starr et al. | 128/205.25 |
| 5,551,419 A | 9/1996 | Froehlich et al. | 128/204.23 |
| 5,551,872 A | 9/1996 | Mena | 433/37 |
| 5,558,090 A | 9/1996 | James | 128/207.18 |
| RE35,339 E | 10/1996 | Rapoport | 128/204.18 |
| 5,560,354 A | 10/1996 | Berthon-Jones et al. | 128/205.25 |
| 5,562,449 A | 10/1996 | Jacobs et al. | 433/215 |
| 5,566,683 A | 10/1996 | Thornton | 128/848 |
| 5,570,704 A | 11/1996 | Buzzard et al. | |
| 5,582,517 A | 12/1996 | Adell | 433/6 |
| 5,592,935 A | 1/1997 | Elstran et al. | 128/205.29 |
| 5,611,485 A | 3/1997 | Davis | 239/8 |
| 5,657,751 A | 8/1997 | Karr, Jr. | 128/205.18 |
| 5,657,752 A | 8/1997 | Landis et al. | 128/207.13 |
| 5,662,101 A | 9/1997 | Ogden et al. | 128/205.25 |
| 5,676,133 A | 10/1997 | Hickle et al. | 128/205.12 |
| 5,678,567 A | 10/1997 | Thornton et al. | 128/848 |
| 5,681,164 A | 10/1997 | Bass | 433/6 |
| 5,687,715 A | 11/1997 | Landis et al. | 128/207.18 |
| 5,713,349 A | 2/1998 | Keaney | 128/204.23 |
| 5,718,244 A | 2/1998 | Thornton | 128/864 |
| 5,718,500 A | 2/1998 | Vinci guerra et al. | 2/431 |
| 5,720,280 A | 2/1998 | Elstran et al. | 128/205.25 |
| 5,720,302 A | 2/1998 | Belfer | 128/848 |
| 5,724,965 A | 3/1998 | Handke et al. | 128/207.13 |
| 5,746,201 A | 5/1998 | Kidd | 128/206.24 |
| 5,752,510 A | 5/1998 | Goldstein | 128/207.18 |
| 5,755,219 A | 5/1998 | Thornton | 128/201.18 |
| 5,807,100 A | 9/1998 | Thornton | 433/48 |
| 5,810,749 A | 9/1998 | Maas | 602/6 |
| 5,829,441 A | 11/1998 | Kidd et al. | 128/848 |
| 5,832,918 A | 11/1998 | Pantino | 128/205.25 |
| 5,846,082 A | 12/1998 | Thornton | 433/215 |
| 5,887,587 A | 3/1999 | Groenke | 128/207.13 |
| 5,891,372 A | 4/1999 | Besset et al. | 264/46.5 |
| 5,954,048 A | 9/1999 | Thornton | 128/201.18 |
| 5,983,892 A | 11/1999 | Thornton | 128/201.26 |
| 5,988,166 A | 11/1999 | Hayek | 128/205.26 |
| 6,012,455 A | 1/2000 | Goldstein | 128/207.18 |
| 6,083,442 A | 7/2000 | Gabilly | 264/163 |
| 6,109,265 A | 8/2000 | Frantz et al. | 128/848 |
| 6,119,694 A | 9/2000 | Correa et al. | 128/207.13 |
| 6,123,071 A | 9/2000 | Berthon-Jones et al. | 128/204.18 |
| 6,155,262 A | 12/2000 | Thornton et al. | 128/859 |
| 6,209,542 B1 | 4/2001 | Thornton | 128/206.29 |
| 6,247,926 B1 | 6/2001 | Thornton | 433/48 |
| 6,263,871 B1 | 7/2001 | Brown et al. | 128/200.29 |
| D448,473 S | 9/2001 | Barnett et al. | D24/110.1 |
| 6,305,376 B1 | 10/2001 | Thornton | 128/848 |
| 6,318,997 B1 | 11/2001 | Mayweather | 433/45 |
| 6,325,064 B1 | 12/2001 | Thornton | 128/204.18 |
| 6,374,824 B1 | 4/2002 | Thornton | 128/201.26 |
| 6,405,729 B1 | 6/2002 | Thornton | 128/848 |
| 6,412,488 B1 | 7/2002 | Barnett et al. | 128/207.13 |
| 6,450,167 B1 | 9/2002 | David et al. | |
| 6,464,924 B1* | 10/2002 | Thornton | 264/331.12 |
| 6,494,206 B1 | 12/2002 | Bergamaschi et al. | 128/206.24 |
| 6,516,805 B1 | 2/2003 | Thornton | 128/848 |
| 6,536,439 B1 | 3/2003 | Palmisano | |
| 6,571,798 B1* | 6/2003 | Thornton | 128/206.21 |
| 6,604,527 B1 | 8/2003 | Palmisano | |
| 6,645,413 B2 | 11/2003 | Jacobs | 264/222 |
| 6,675,802 B1 | 1/2004 | Thornton | 128/206.29 |
| 6,758,212 B2 | 7/2004 | Swann | |
| 6,769,910 B1 | 8/2004 | Pantino | |
| 6,845,774 B2 | 1/2005 | Gaskell | 128/848 |
| 6,857,428 B2 | 2/2005 | Thornton | 128/206.21 |
| 6,877,513 B2 | 4/2005 | Scarberry et al. | 128/848 |
| 7,077,138 B2 | 7/2006 | Bateman et al. | 128/206.14 |
| 7,174,895 B2 | 2/2007 | Thornton et al. | 128/848 |
| 7,597,103 B2 | 10/2009 | Thornton et al. | |
| 7,748,386 B2 | 7/2010 | Thornton | |
| 7,832,403 B2 | 11/2010 | Halstrom et al. | |
| 7,909,035 B2 | 3/2011 | Thornton | |
| 2002/0000230 A1 | 1/2002 | Gaskell | |
| 2002/0129818 A1 | 9/2002 | Morgan et al. | 128/206.26 |
| 2002/0139366 A1 | 10/2002 | Gaschke | |
| 2003/0217753 A1 | 11/2003 | Thornton | |
| 2004/0079374 A1 | 4/2004 | Thornton | |
| 2004/0226563 A1 | 11/2004 | Xu et al. | |
| 2004/0237965 A1 | 12/2004 | Bibi et al. | 128/206.29 |
| 2005/0016544 A1 | 1/2005 | Thornton | 128/207.18 |
| 2006/0005837 A1 | 1/2006 | Thornton | 128/205.25 |
| 2006/0023228 A1 | 2/2006 | Geng | |
| 2006/0124131 A1 | 6/2006 | Chandran et al. | 128/206.28 |
| 2007/0006879 A1 | 1/2007 | Thornton | |
| 2007/0125388 A1 | 6/2007 | Thornton | 128/848 |
| 2008/0006273 A1 | 1/2008 | Thornton | 128/206.21 |
| 2008/0006274 A1 | 1/2008 | Thornton | |
| 2008/0032256 A1 | 2/2008 | Thornton | 433/57 |
| 2008/0060648 A1 | 3/2008 | Thornton et al. | |

FOREIGN PATENT DOCUMENTS

| | | |
|---|---|---|
| EP | 0 312 368 A1 | 4/1989 |
| EP | 0 359 135 A1 | 3/1990 |
| FR | 2731624 | 9/1996 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/20924 | 5/1998 |
| WO | WO 98/26736 | 6/1998 |
| WO | WO 98/46177 | 10/1998 |

OTHER PUBLICATIONS

Acurest, The Logic Sleep Mask http://sleepapneamasks.com.au/, 2002.

Whitestone et al., Fabrication of Total Contract Burn Masks Using Non-Contact Surface Scanning: A New Standard of Care, 1997, pp. 1-8.

Personally Moulded Sleep Apnea Masks, http://web.archive.org/web/20030618145716/www.sleepapneamasks.com.au/default.asp, downloaded Aug. 17, 2009.

Photocopies of 2-piece dental device manufactured by Currie-Gibson Dental Laboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 3 pages.

Great Lakes Orthodontics, Ltd.; *Nocturnal Airway Patency Appliance*; 2 pages.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

"Donning the Mask," Dräger: X-plore 5500.2006.Dräger Safety, http://www.draeger-usa.com/ST/internet/pdf/US/protection/AnlegiPO_X-plore_5500_US.pdf, 2 pages, accessed Sep. 14, 2006.

PCT Notification of Transmittal of the International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT Notification of Transmittal of the International Search Report and the Written Opinion of the International Searching Authority, or the Declaration, PCT/US 06/26622, 10 pages, mailing date Feb. 21, 2007.

Thornton, "Oral Appliance for Treating a Breathing Condition," U.S. Appl. No. 11/278,918, pending, 42 pages, filed Apr. 6, 2006.

European Patent Office Communication, Application No. 03 809 555.0-1257, Applicant: W. Keith Thornton, 4 pages, dated Aug. 7, 2009.

Mayo Clinic Health Letter; Reliable Information for a Healthier Life; *Snoring: Laser Surgery Joins Battle to Restore Peace and Quiet*; vol. 13, No. 7, 8 pages, Jul. 1995.

Schmidt-Nowara, et al.; An American Sleep Disorders Association Review; *Oral Appliances for the Treatment of Snoring and Obstructive Sleep Apnea: A Review*; pp. 501-510, 1995.

CPAP-PRO—Introducing a New Comfort Level for CPAP Users brochure, 2 pages.

W. Keith Thornton, "Multi-Chamber Mask and Method of Forming the Same," U.S. Appl. No. 11/428,933, filed Jul. 6, 2006.

W. Keith Thornton, "Stability Medical Mask," U.S. Appl. No. 11/853,343, currently pending, filed Sep. 11, 2007.

W. Keith Thornton, "System and Method for Custom-Orientihng a Medical Mask to an Oral Appliance," U.S. Appl. No. 11/947,291, currently pending, filed Nov. 29, 2007.

PCT, Notification of Transmittal of the International Search Report and the Written Opinion of the International Searching Authority, or the Declaration, PCT/US06/26622, 11 pages, Date Mailed: Feb. 21, 2007.

Canadian Intellectual Property Office, Application No. 2,502,280, Applicant: W. Keith Thornton, 3 pages, dated Feb. 23, 2010.

Craig, William H., et al.; "Skeletal class II treatment with the Chateau appliance," The Journal of Pedondontics (vol. 11:120); pp. 120-138, 1987.

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages.

* cited by examiner

SYSTEM AND METHOD FOR FORMING A CUSTOM MEDICAL MASK USING AN ORIENTATION DEVICE

RELATED APPLICATION

This application claims the benefit under 35 U.S.C. §119(e) of U.S. Provisional Application Ser. No. 60/806,662 filed Jul. 6, 2006.

TECHNICAL FIELD

This invention relates generally to masks for use in medical and other clinical applications, and more particularly to a system and method for forming a custom medical mask using an orientation device.

BACKGROUND

Many people experience breathing problems on a recurring basis, which often result in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included face masks, nose masks, or nasal inserts that help deliver air to the user's nose at positive pressure. These devices help force open the user's breathing passage and thereby improve the user's breathing. However, previous devices have often provided an inadequate fit and thus have caused discomfort for users and failed to adequately prevent leakage.

OVERVIEW

According to one embodiment, a method for use in forming a custom medical mask for a particular user includes, while an oral appliance is positioned in the particular user's mouth to receive the particular user's teeth and is coupled to an orientation device using a post of the oral appliance, applying an impression material over the orientation device and the particular user's face including at least the particular user's mouth and a portion of the particular user's nose surrounding the particular user's nostrils, such that the impression material conforms to the orientation device and to the particular user's unique facial features. The impression material may be removed from the particular user's face together with the orientation device. A cast of the particular user's face may be created using the impression material together with the orientation device as a mold, such that the cast conforms to the impression material and the orientation device. A deformable material may be applied to the cast of the particular user's face to form a custom medical mask for the particular user, such that the deformable material conforms to the cast. The custom medical mask may be custom-fitted to the particular user's unique facial features and custom-oriented to the particular user's teeth.

According to another embodiment, a system for use in forming a custom medical mask for a particular user includes an oral appliance, an orientation device, and an impression material. The oral appliance includes an upper arch configured to be positioned within a particular user's mouth to receive the particular user's upper teeth and a post coupled to the upper arch and configured to protrude from the particular user's mouth when the upper arch is positioned within the particular user's mouth. The orientation device includes an elongated tubular member configured to receive the oral appliance post to couple the orientation device to the oral appliance and a restraining structure configured to substantially limit the movement of the orientation device relative to the oral appliance. The impression material is conformed to the orientation device and the particular user's unique facial features and custom-oriented to the particular user's teeth via the orientation device and the oral appliance.

According to another embodiment, a custom medical mask includes a deformable thermoplastic polymer and a locking mechanism. The deformable thermoplastic polymer is conformed to a custom mold of the particular user's unique facial features and custom-fitted to the particular user's unique facial features, the particular user's unique facial features including portions of the particular user's face surrounding the particular user's mouth and at least portions of the particular user's nose, having been formed using a custom mold of the particular user's unique facial features. The locking mechanism is configured to receive and secure a post of an oral appliance to maintain a custom orientation between the oral appliance and the custom-fitted thermoplastic polymer.

Certain embodiments may provide one or more technical advantages. Certain embodiments may provide a custom medical mask that conforms substantially optimally to a user's unique facial features. Certain embodiments may provide a custom medical mask that may couple to an oral appliance to provide an improved fit based on the precise custom orientation or positional relationship between a user's unique facial structure and the user's teeth. Certain embodiments may provide a process for use in forming a custom medical mask that maintains a precise custom orientation or positional relationship between a user's unique facial features and the user's teeth through each step of the process to ensure that the custom medical mask has an optimal fit, customized for the user. Certain embodiments may provide improved fit, increased comfort, reduced leakage, and improved performance, whether for treating sleep disordered breathing, administering anesthesia, or any other suitable purpose for which the custom medical mask is used. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which.

DESCRIPTION OF EXAMPLE EMBODIMENTS

Figure 1A:
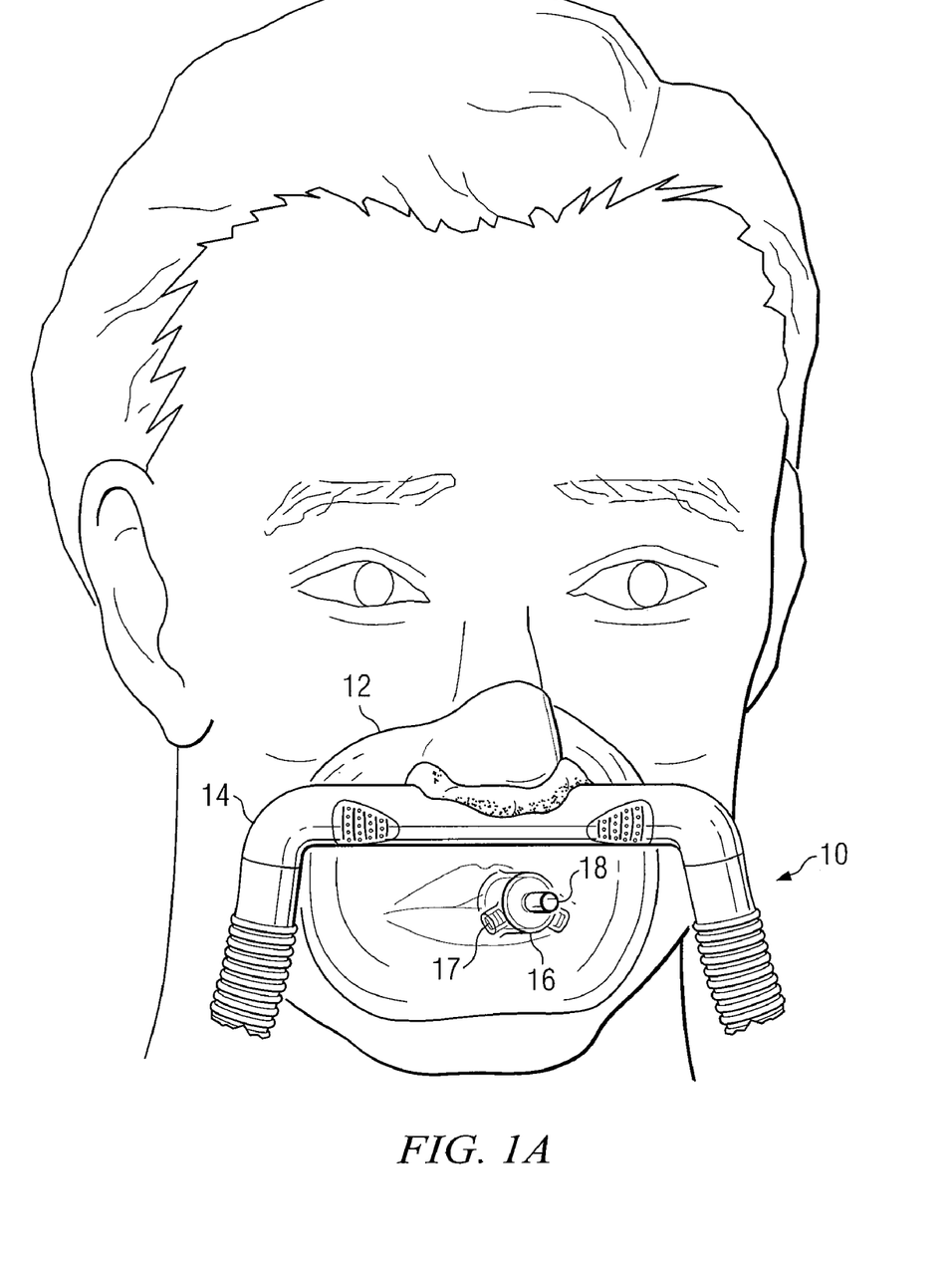
FIGS. 1A and 1B illustrate an example custom medical mask.
Figure 1B:
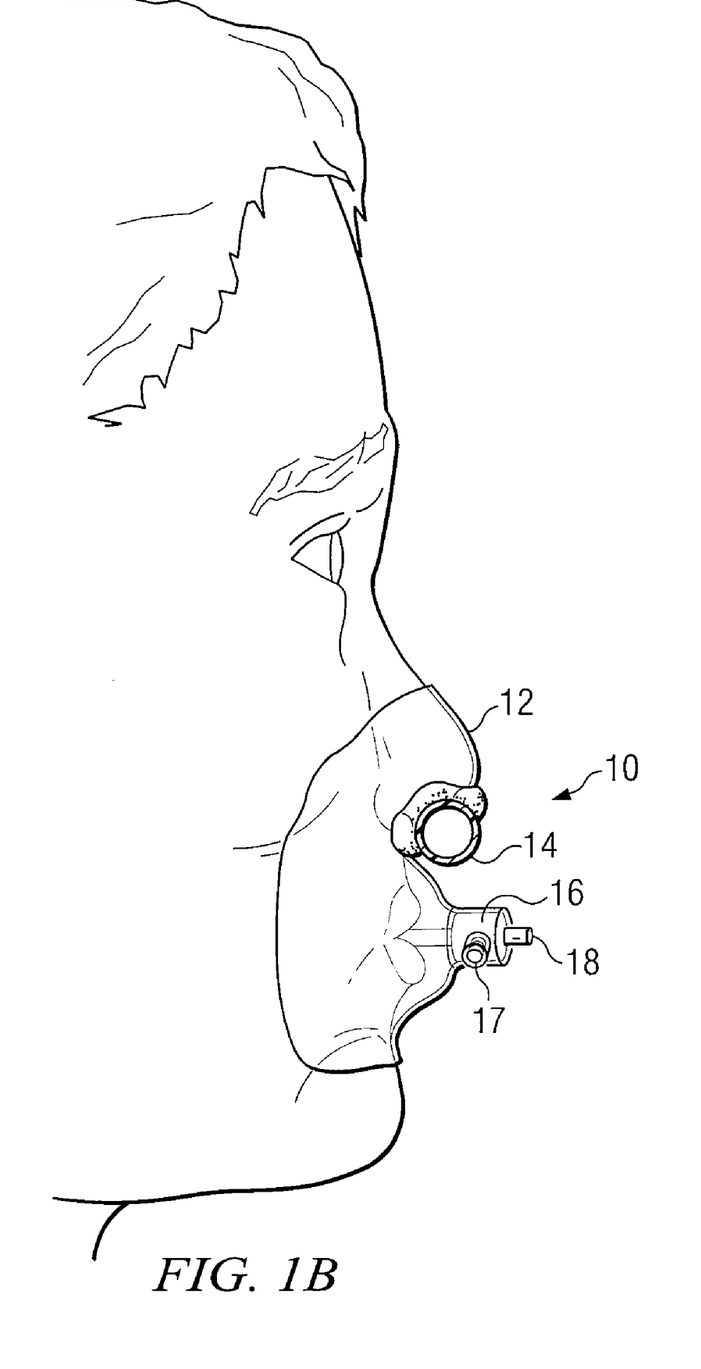

FIGS. 1A and 1B illustrate an example custom medical mask 10, customized for a particular user. Custom medical mask 10 is a mask custom formed for the particular user and suited to assist in a medical treatment or therapy for the particular user. Generally, a precise orientation or positional relationship exists between a user's unique facial features and the user's teeth that is substantially fixed and stable. Custom medical mask 10 may be formed using an impression of the particular user's unique facial features and an orientation device to establish an optimal fit, customized for the particular user, based in part on the precise orientation or positional relationship between the particular user's unique facial features and the particular user's teeth. Custom medical mask 10 may conform substantially optimally to the particular user's unique facial features. Custom medical mask 10 may couple to an oral appliance to maintain a custom orientation or positional relationship between custom medical mask 10 and the particular user's teeth. In certain embodiments, custom medical mask 10 may include body 12, fitting 14, and locking mechanism 16.

In certain embodiments, body 12 may be formed from a thin sheet of deformable material configured to cover at least a portion of the particular user's face. Body 12 may be configured to cover the particular user's mouth and at least a portion of the particular user's nose surrounding the nostrils. In a particular embodiment, body 12 may be configured to cover only the soft cartilaginous portions of the particular user's nose and portions of the particular user's face to the sides of and below the soft cartilaginous portions of the nose, but not to cover the hard bony portions of the nose generally above the soft cartilaginous portions of the nose. Body 12 may be formed from a single sheet of deformable material or may be formed from multiple sheets of deformable material coupled to one another.

In certain embodiments, body 12 may include a suitable thermoplastic polymer and suitable fillers, stabilizers, coloring agents, antioxidants, antimicrobial agents, and/or other materials. In certain embodiments, body 12 may include a light curing material such as the material sold under the name TRIAD by DENTSPLY INTERNATIONAL INC. Such materials are known in various contexts to those skilled in the art.

In a particular embodiment, body 12 may include, possibly in addition to one or more other materials, one or more of the thermoplastic polycaprolactone polymers or other aliphatic polyesters described in U.S. Pat. Nos. 4,784,123 and 5,112,225 and product literature of UNION CARBIDE CORPORATION. One or more polycaprolactone polymers may have the formula:

(1)

where R is an aliphatic hydrocarbon and n may range between approximately 300 to approximately 650. However, the present invention contemplates using any suitable polycaprolactone polymer.

For example, body 12 may include one or more of the TONE P-700, TONE P-767, or TONE P-787 polycaprolactone polymers manufactured by UNION CARBIDE CORPORATION, singly or in any combination. In a particular example, body 12 may include approximately thirty parts by volume of TONE P-700 and sixty parts by volume of TONE P-767, together with approximately ten parts by volume of one or more other polymers, depending upon the application and particular needs.

TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

(2)

where R is an aliphatic hydrocarbon. In general, polycaprolactone polymers may display desirable dimensional stability and thermoplasticity during cooling, biocompatibility, and a variety of other characteristics making them suitable for use in forming embodiments of custom medical mask 10.

In certain embodiments, fitting 14 may include any suitable structure to connect custom medical mask 10 to a suitable clinical gas delivery system. For example, fitting 14 may represent an acrylic, male-type hose connector that couples to an opening in body 12. As another example, fitting 14 may represent a gasket surrounding an opening into body 12. Fitting 14 may include a structure configured to connect custom medical mask 10 to multiple hoses. A suitable clinical gas delivery system may be a Continuous Positive Air Pressure (CPAP) system, a Bilevel Positive Air Pressure (BiPAP) system, or other system configured to deliver air, oxygen, anesthetic, or other gases to the particular user wearing custom medical mask 10.

Locking mechanism 16 may represent one or more structures configured to couple and secure custom medical mask 10 to an oral appliance 20. In certain embodiments, locking mechanism 16 may represent a sleeve with an opening configured to receive a post 18 of oral appliance 20 to couple custom medical mask 10 to oral appliance 20. Locking mechanism 16 may further include one or more threaded openings configured to receive one or more set screws 17 to retain post 18 of oral appliance 20 within locking mechanism 16.

FIGS. 2A through 2J illustrate example devices and steps for use in forming custom medical mask 10 for the particular user. In certain embodiments, one or more of these devices and steps may be used to form a custom medical mask 10 that maintains a precise custom orientation or positional relationship between the particular user's unique facial features and the particular user's teeth through each step of the forming process to ensure that custom medical mask 10 has an optimal fit, customized for the particular user. Certain embodiments of custom medical mask 10 formed using one or more of these devices and steps may provide improved fit, increased comfort, reduced leakage, and improved performance, whether for treating sleep disordered breathing, administering anesthesia, or any other suitable purpose for which custom medical mask 10 is used.

Figure 2A:
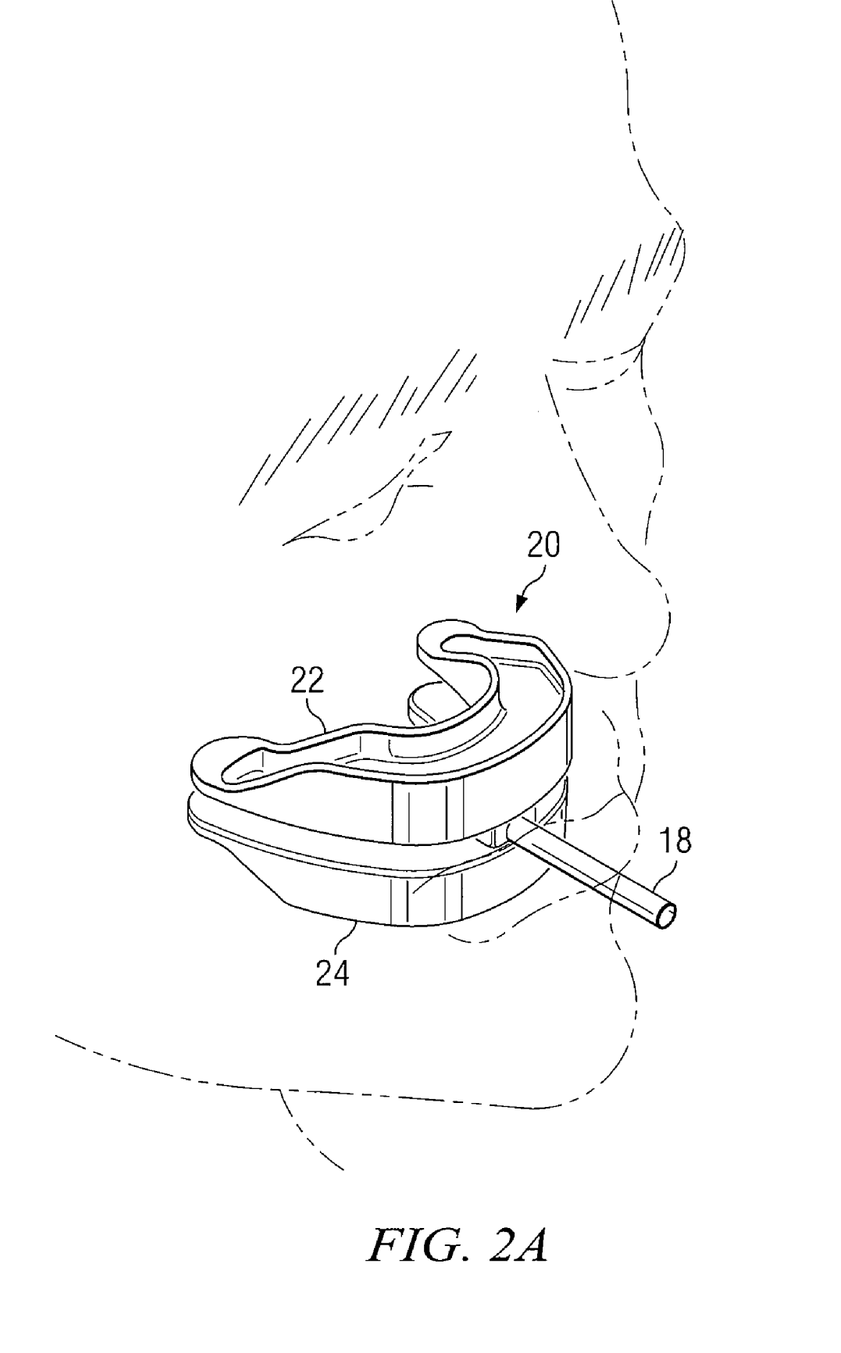
FIGS. 2A through 2J illustrate example devices and steps for use in forming a custom medical mask.

As shown in FIG. 2A, oral appliance 20 with post 18 may be inserted into the particular user's mouth. In certain embodiments, oral appliance 20 may include upper arch 22 and lower arch 24. Upper arch 22 may be configured to receive the particular user's upper teeth. Lower arch 24 may be configured to receive the particular user's lower teeth. As used herein, reference to the particular user's teeth is meant to include any one or more of the user's teeth depending on the structure of the oral appliance. Oral appliance 20 may include one or more structures configured to couple upper arch 22 to lower arch 24. For example, these one or more structures may be configured to position lower arch 24 relative to upper arch 22 to define a particular position for the particular user's lower jaw relative to the particular user's upper jaw. In certain embodiments, oral appliance 20 may represent a bite register or wax mold suitable to receive either or both of the particular user's upper and lower teeth.

In certain embodiments, post 18 may represent one or more structures configured to project out of the particular user's mouth when oral appliance 20 is positioned in the particular user's mouth. In a particular embodiment, post 18 may represent a substantially straight, cylindrical projection that may be greater than one inch in length. Post 18 may have a substantially circular, square, or any other appropriately shaped cross-section. One or more components of oral appliance 20 may be custom-shaped to fit to the particular user's unique dental structure. Oral appliance 20 with post 18 may serve to register or define an orientation or positional relationship relative to the particular user's teeth. In certain embodiments, post 18 may be removable from oral appliance 20.

Figure 2B:
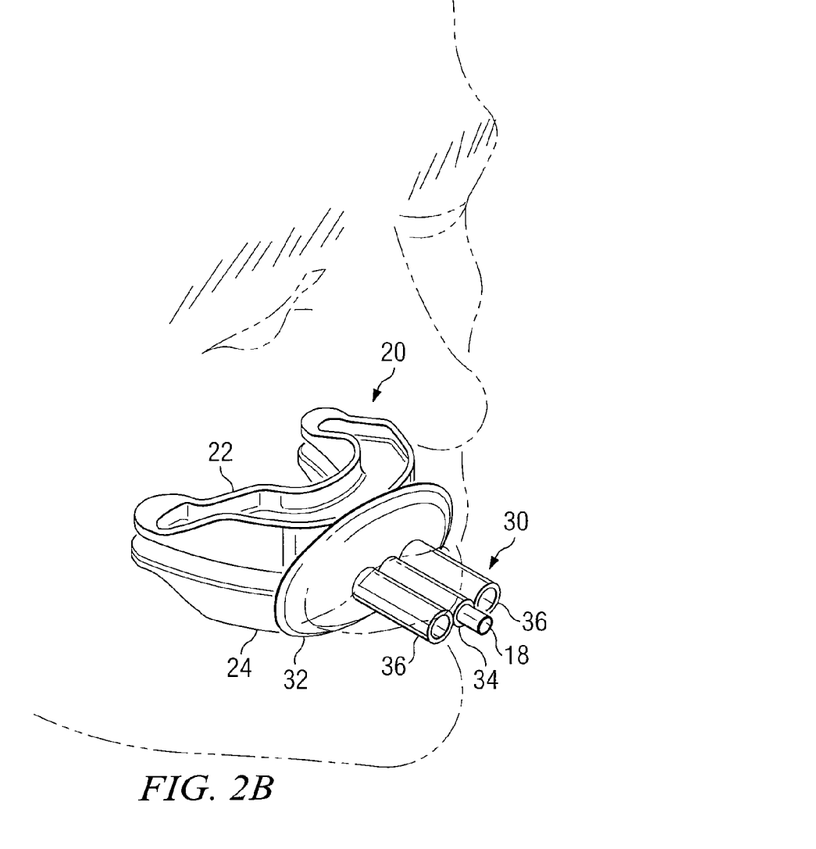

Orientation device 30 may represent one or more structures configured to define and maintain a precise custom orientation or positional relationship between the particular user's unique facial features and the particular user's teeth during the fabrication of custom medical mask 10. As shown in FIG. 2B, orientation device 30 may be coupled to post 18 of oral appliance 20 when oral appliance 20 is positioned within the particular user's mouth to establish an orientation or positional relationship between orientation device 30 and the particular user's teeth. Orientation device 30 may be coupled to oral appliance 20 prior to or subsequent to the positioning of oral appliance 20 in the particular user's mouth.

Figure 3A:
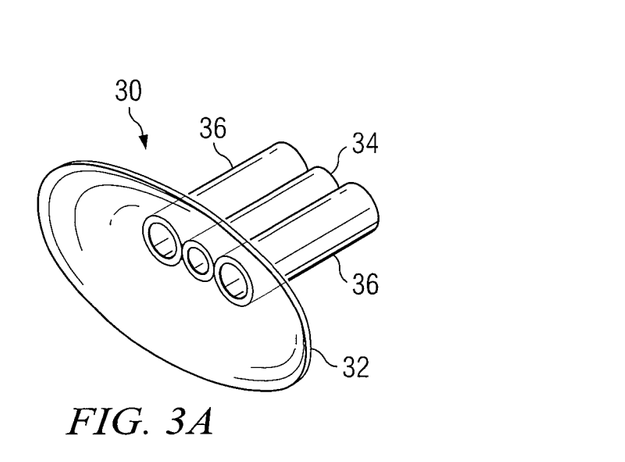
FIGS. 3A and 3B illustrate an example orientation device for use in forming a custom medical mask.
Figure 3B:
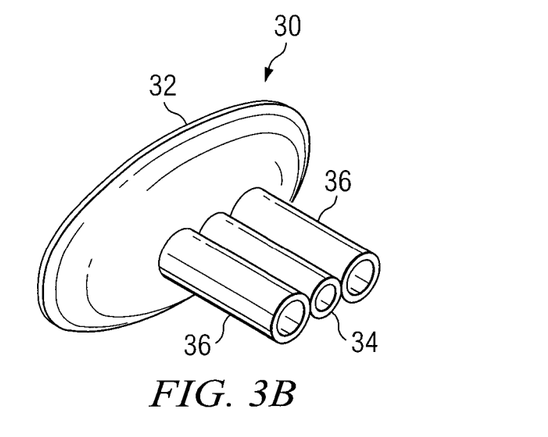

FIGS. 3A and 3B illustrate an example orientation device 30 for use in forming custom medical mask 10. In certain embodiments, orientation device 30 may include sleeve 34, one or more breathing tubes 36, and a restraining structure, such as lip shield 32. Sleeve 34 represents a structure configured to align orientation device 30 with post 18 of oral appliance 20. In a particular embodiment, sleeve 34 may represent a cylindrical tube configured to receive post 18. Although shown in FIGS. 3A and 3B with a substantially circular cross-section, in alternative embodiments sleeve 34 may have a square or other suitable cross-section to align orientation device 30 with post 18. In embodiments of orientation device 30 that include one or more breathing tubes 36, breathing tube 36 may provide a channel through which the particular user may breathe. In embodiments of orientation device 30 that include a restraining structure, such as lip shield 32, the restraining structure may operate to restrain orientation device 30 from moving from a selected position along the length of post 18. For example, lip shield 32 may represent one or more structures configured to be positioned between the particular user's teeth and lips to restrain orientation device 30. As a more particular example, lip shield 32 may represent a flange projecting in a direction generally perpendicular to the long axis of sleeve 34.

Figure 2C:
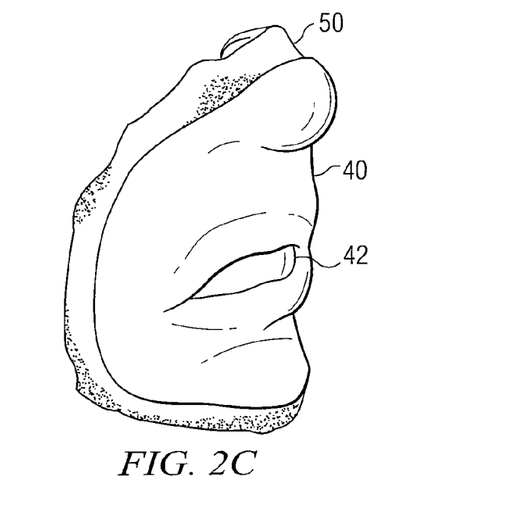

FIG. 2C illustrates an example mask mold 40 with impression material 50 for use in forming custom medical mask 10. In certain embodiments, mask mold 40 may be used together with impression material 50 to create an impression of certain unique physical features of the particular user's face. For example, mask mold 40 may represent a tray that may be generally shaped to conform to at least a portion of a generic user's face. Mask mold 40 may include one or more plastics, acrylics, or other appropriate materials. Mask mold 40 may include an opening 42 corresponding to the location of a generic user's mouth. Impression material 50 may represent a deformable material used to create an impression of at least a portion of the particular user's face. In a particular embodiment, impression material 50 may include a dental irreversible alginate or other appropriate material used to create impressions. In operation, impression material 50 may be applied to at least a portion of the inside surface of mask mold 40.

Figure 2D:
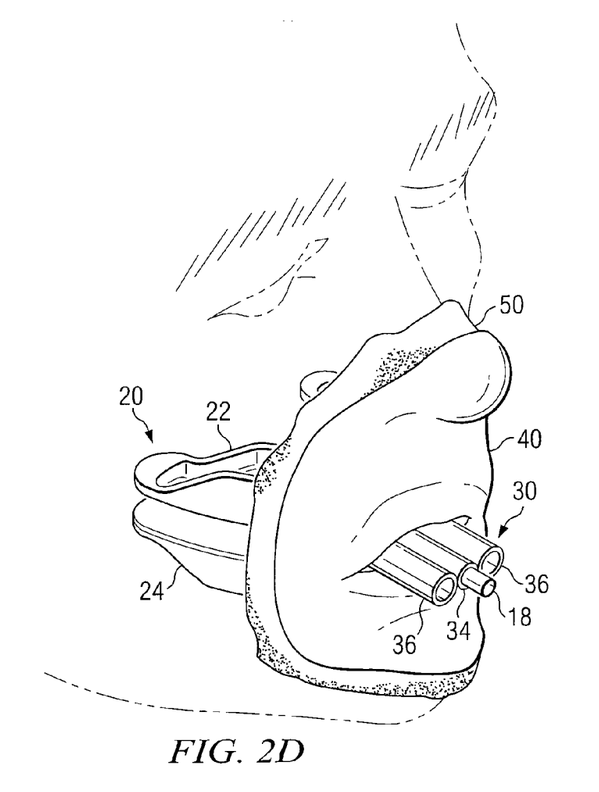

As shown in FIG. 2D, mask mold 40 with impression material 50 may then be applied to the particular user's face, while oral appliance 20 is positioned in the particular user's mouth and coupled to orientation device 30. Alternatively, impression material 50 may be applied directly to the particular user's face without the use of mask mold 40. Impression material 50 may conform to at least a portion of orientation device 30. An interior surface of impression material 50 directly or indirectly contacts the particular user's face and conforms to the particular user's unique facial features. As a result, impression material 50 may establish a precise custom orientation or positional relationship between the conformed interior surface of impression material 50 and orientation device 30, which further establishes a precise custom orientation or positional relationship between the conformed interior surface of impression material 50 and oral appliance 20, thereby establishing a precise custom orientation or positional relationship between the conformed interior surface of impression material 50 and the particular user's teeth. As impression material 50 becomes firm, impression material 50 may retain these established orientations or positional relationships.

Figure 2E:
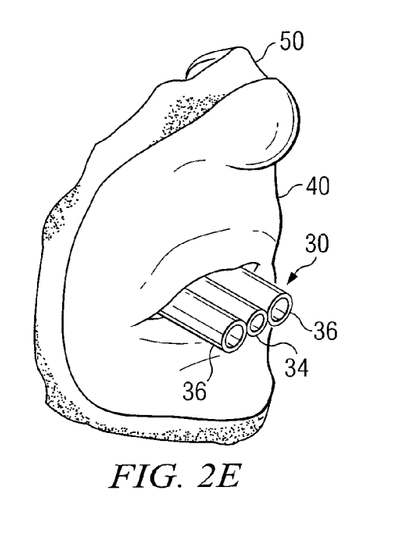

As shown in FIG. 2E, once impression material 50 has become firm enough to retain the impression of the particular user's face, impression material 50 together with mask mold 40 and orientation device 30 may be removed from the particular user's face, such that the orientation or positional relationship between the conformed interior surface of impression material 50 and orientation device 30 is maintained.

Figure 2F:
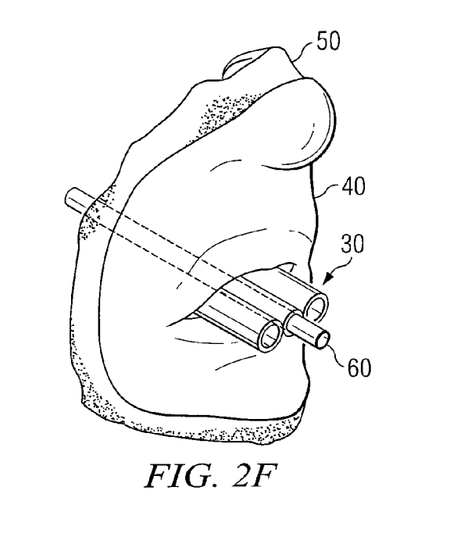

As shown in FIG. 2F, after impression material 50, mask mold 40, and orientation device 30, have been removed, post 60 may be inserted into sleeve 34 of orientation device 30. Post 60 represents one or more structures that correspond to post 18 of oral appliance 20. In certain embodiments, post 18 may be removed from oral appliance 20 with orientation device 30 when impression material 50 and mask mold 40 are removed from the particular user's face and used as post 60. In certain embodiments, post 60 may be a structure, separate from post 18, with a shape the same as or substantially similar to the shape of post 18. In an alternative embodiment, post 60 may be integral to orientation device 30. Impression material 50 together with orientation device 30 and post 60 may be used to create a cast of at least a portion of the particular user's face. For example, a cast of at least a portion of the particular user's face may be created using impression material 50 as a mold for the cast. In certain embodiments, an exterior surface of cast 70 conforms to a portion of the interior surface of impression material 50 and cast 70 couples to orientation device 30, such that an orientation or positional relationship is established between the conformed exterior surface of cast 70 and orientation device 30 based on the orientation or positional relationship between the interior surface of impression material 50 and orientation device 30.

Figure 2G:
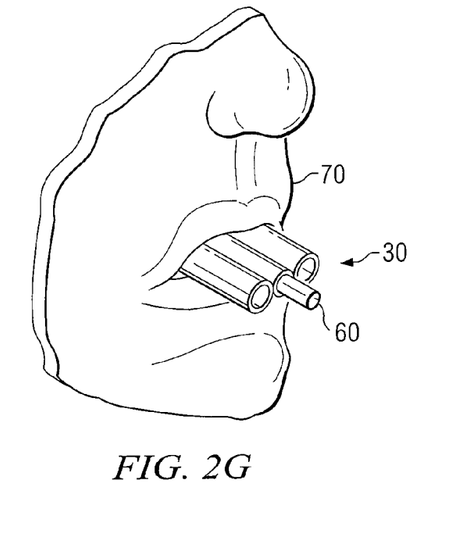
Figure 2H:
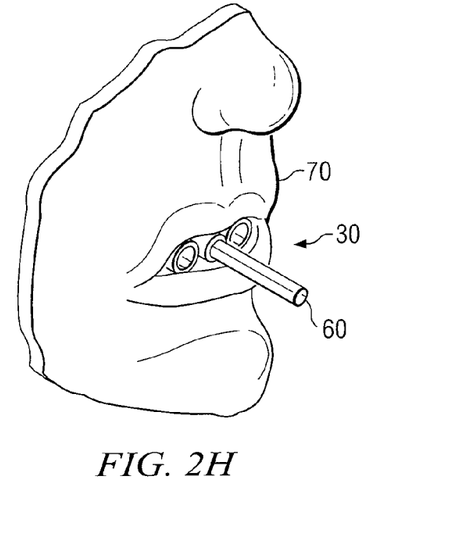

FIG. 2G illustrates an example cast 70 of a portion of the particular user's face. In certain embodiments, cast 70 includes orientation device 30 with post 60. Cast 70 may include any appropriate casting material, such as a suitable dental plaster or stone. Portions of orientation device 30 may be trimmed or otherwise removed, as shown in FIG. 2H.

Figure 2I:
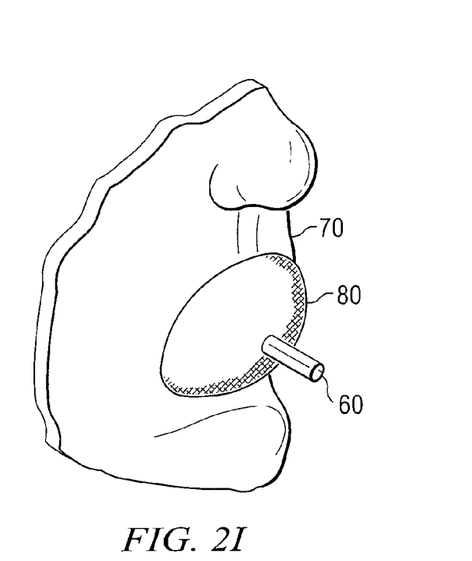

As shown in FIG. 2I, in certain embodiments, chamber mold 80 may represent one or more materials applied to cast 70 to model an open chamber in the region surrounding the particular user's mouth and lips. Chamber mold 80 may provide for the creation of an oral chamber in custom medical mask 10 when cast 70 is used to create custom medical mask 10. An oral chamber in custom medical mask 10 may be advantageous for allowing movement of the particular user's mouth and/or lips when the particular user is wearing custom medical mask 10.

Figure 2J:
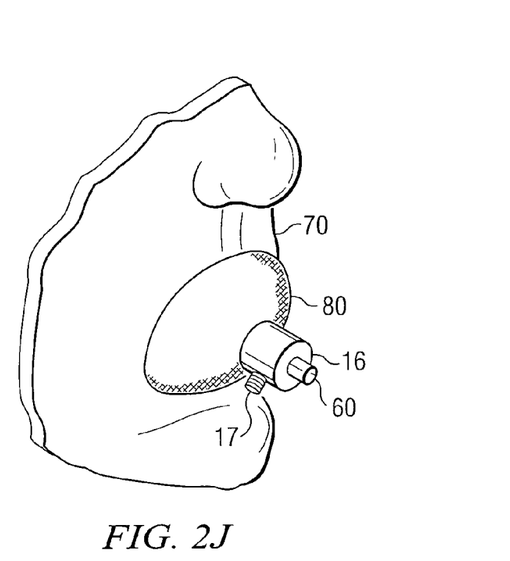

As shown in FIG. 2J, in certain embodiments, locking mechanism 16 may be coupled to post 60. For example, post 60 may be received and secured within locking mechanism 16. In certain embodiments, post 60 may be secured within locking mechanism 16 by adjusting one or more set screws 17 to contact and apply pressure to post 60.

Figure 2K:
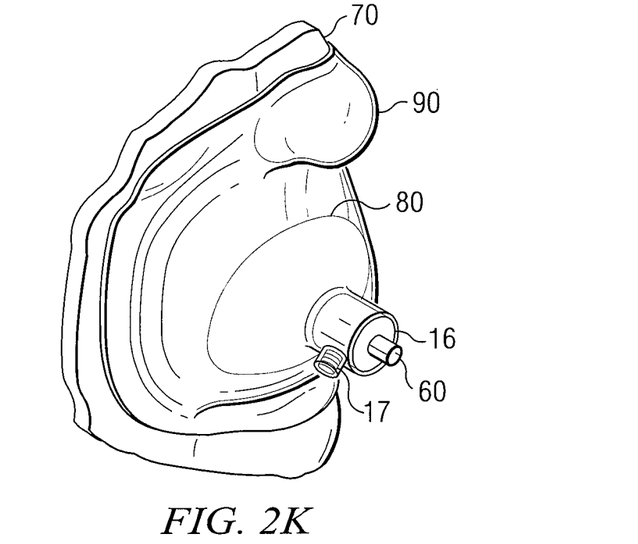

As shown in FIG. 2K, in certain embodiments, one or more pieces of thin deformable material 90 may be applied to cast 70 to form body 12 of custom medical mask 10. An interior surface of deformable material 90 may directly or indirectly contact cast 70 and conform to the conformed exterior surface of cast 70. In certain embodiments, deformable material 90 may conform to post 60, with or without locking mechanism 16, and may establish an orientation or positional relationship between the conformed interior surface of deformable material 90 and post 60 and/or locking mechanism 16, further establishing an orientation or positional relationship between the conformed interior surface of deformable material 90 and orientation device 30. In embodiments in which deformable material 90 is allowed to conform to post 60 without locking mechanism 16, locking mechanism 16 may subsequently be coupled to post 60 and one or more additional pieces of thin deformable material 90, or other appropriate material, may be applied to conform to locking mechanism 16.

In certain embodiments, a thin piece of deformable material 90 applied to cast 70 may be a mask blank as described in U.S. Pat. No. 6,857,428. As one example, an appropriate thin piece of deformable material 90 may be obtained from CHESAPEAKE MEDICAL PRODUCTS, INC.

Prior to applying the one or more pieces of thin deformable material 90 to cast 70, the material is placed in a deformable state. For example, where the deformable material 90 includes one or more polycaprolactone polymers, the deformable material 90 may be heated in a microwave oven, in water or other non-solvent neutral liquid, or in any other suitable manner to between approximately 140° F. and approximately 180° F. so as to place deformable material 90 in a deformable state. While in a deformable state, deformable material may be pressed against or otherwise allowed to conform to the shape of cast 70 to form custom medical mask 10. As deformable material 90 cools and hardens, custom medical mask 10 solidifies and will retain its custom shape. In confirming to cast 70, an interior surface of custom medical mask 10 also conforms to the particular user's unique facial features. As a result, the conformed interior surface of custom medical mask 10 has the same orientation or positional relationship to oral appliance 20 (and thus to the particular user's teeth) that the conformed interior surface of impression material 50 had to oral appliance 20 (and thus to the particular user's teeth).

Through the use of the methods and devices described above, a custom medical mask 10 may be formed substantially optimally for the particular user's unique facial features. For example, custom medical mask 10 may have an interior surface that conforms substantially to the particular user's unique facial features, such that the conformed interior surface of the custom medical mask 10 has substantially the same orientation or positional relationship to the particular user's teeth as the conformed interior surface of impression material 50 had to the particular user's teeth at the time that impression material 50 was applied to the particular user's face. Custom medical mask 10 may be custom formed at least in part through the maintenance of relationships (1) from the particular user's teeth to oral appliance 20, and from oral appliance 20 to orientation device 30, and (2) from the particular user's unique facial features to impression material 50, from impression material 50 to orientation device 30, from impression material 50 and orientation device 30 to cast 70, and from orientation device 30 and cast 70 to deformable material 90, which forms body 12 of custom medical mask 10. Thus, by maintaining these relationships, the precise orientation or positional relationship between the particular user's teeth and the particular user's unique facial features may be utilized to form custom medical mask 10, which may provide improved fit, increased comfort, reduced leakage, and improved performance, whether for treating sleep disordered breathing, for administering anesthesia, or for any other suitable purpose for which the custom medical mask 10 is used.

Although the present invention has been described in several embodiments, a plenitude of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A method of forming a custom medical mask for a particular user, comprising:
while an oral appliance is positioned in the particular user's mouth to receive the particular user's teeth and is coupled to an orientation device using a post of the oral appliance, applying an impression material over the orientation device and the particular user's face including at least the particular user's mouth and a portion of the particular user's nose surrounding the particular user's nostrils, such that the impression material conforms to the orientation device and to the particular user's unique facial features;
removing the impression material from the particular user's face together with the orientation device,
creating a cast of the particular user's face using the impression material together with the orientation device as a mold, such that the cast conforms to the impression material and the orientation device; and
applying a deformable material to the cast of the particular user's face to form a custom medical mask for the particular user, such that the deformable material conforms to the cast;
wherein the custom medical mask is custom-fitted to the particular user's unique facial features and custom-oriented to the particular user's teeth; and
wherein the orientation device comprises at least one breathing passage configured to allow the particular user to breathe through the particular user's mouth when the particular user's mouth is covered with the impression material.

2. The method of claim 1, further comprising inserting into the orientation device a second post corresponding to the oral appliance post, prior to applying the deformable material, such that when the deformable material is applied to the cast the deformable material further conforms to the second post within the orientation device.

3. The method of claim 2, further comprising coupling a locking mechanism to the second post, prior to applying the deformable material, such that when the deformable material is applied to the cast the deformable material further conforms to the locking mechanism.

4. The method of claim 1, further comprising removing the impression material from the particular user's face together with the orientation device and the post of the oral appliance, such that when the deformable material is applied to the cast the deformable material further conforms to the post of the oral appliance.

5. The method of claim 4, further comprising coupling a locking mechanism to the post of the oral appliance, prior to applying the deformable material, such that when the deformable material is applied to the cast the deformable material further conforms to the locking mechanism.

6. The method of claim 1, wherein the orientation device comprises:
   an elongated tubular member configured to receive the oral appliance post; and
   a restraining structure configured to limit movement of the orientation device relative to the oral appliance.

7. The method of claim 6, wherein the restraining structure comprises a flange projecting from the elongated tubular member and configured to be positioned between the particular user's lips and teeth.

8. The method of claim 1, wherein the deformable material comprises a thermoplastic polymer and is heated to transition to a deformable state prior to applying the deformable material to the cast.

9. The method of claim 8, wherein the thermoplastic polymer comprises a polycaprolactone polymer.

10. The method of claim 1, further comprising:
    creating openings in the custom medical mask corresponding to the particular user's nostrils; and
    coupling a fitting for a clinical gas delivery system to the custom medical mask for supplying a gas to the particular user's nostrils through the openings in the custom medical mask.

11. A method for forming a cast for use in forming a custom medical mask for a particular user, comprising:
    while an oral appliance is positioned in the particular user's mouth to receive the particular user's teeth and is coupled to an orientation device using a post of the oral appliance, applying an impression material over the orientation device and the particular user's face including at least the particular user's mouth and a portion of the particular user's nose surrounding the particular user's nostrils, such that the impression material conforms to the orientation device and to the particular user's unique facial features;
    removing the impression material from the particular user's face together with the orientation device; and
    creating a cast of the particular user's face using the impression material together with the orientation device as a mold, such that the cast conforms to the impression material and the orientation device;
    wherein the orientation device comprises at least one breathing passage configured to allow the particular user to breathe through the particular user's mouth when the particular user's mouth is covered with the impression material.

12. The method of claim 11, wherein the orientation device comprises:
    an elongated tubular member configured to receive the oral appliance post; and
    a restraining structure configured to limit movement of the orientation device relative to the oral appliance.

13. The method of claim 12, wherein the restraining structure comprises a flange projecting from the elongated tubular member and configured to be positioned between the particular user's lips and teeth.

* * * * *